United States Patent
Hovorka

(10) Patent No.: US 9,089,305 B2
(45) Date of Patent: Jul. 28, 2015

(54) SUBSTANCE MONITORING AND CONTROL IN HUMAN OR ANIMAL BODIES

(75) Inventor: Roman Hovorka, Cambridge (GB)

(73) Assignee: CAMBRIDGE ENTERPRISE LIMITED, Cambridgeshire (GB)

( * ) Notice: Subject to any disclaimer, the term of this patent is extended or adjusted under 35 U.S.C. 154(b) by 1084 days.

(21) Appl. No.: 13/133,335

(22) PCT Filed: Dec. 8, 2009

(86) PCT No.: PCT/GB2009/051671
§ 371 (c)(1),
(2), (4) Date: Jun. 23, 2011

(87) PCT Pub. No.: WO2010/067112
PCT Pub. Date: Jun. 17, 2010

(65) Prior Publication Data
US 2011/0257627 A1 Oct. 20, 2011

(30) Foreign Application Priority Data
Dec. 9, 2008 (GB) .................................. 0822374.5

(51) Int. Cl.
*A61B 5/00* (2006.01)
*A61B 5/145* (2006.01)
(Continued)

(52) U.S. Cl.
CPC ........... *A61B 5/4839* (2013.01); *A61B 5/14532* (2013.01); *A61M 5/1723* (2013.01);
(Continued)

(58) Field of Classification Search
CPC .................. A61M 2005/14208; A61M 5/172; A61M 5/1723; A61B 5/4839; G06F 19/3468

USPC ....................................................... 604/65–67
See application file for complete search history.

(56) References Cited

U.S. PATENT DOCUMENTS

| 7,785,313 B2 * | 8/2010 | Mastrototaro ................ 604/503 |
| 2003/0050621 A1 | 3/2003 | Lebel et al. |
| 2003/0060753 A1 | 3/2003 | Starkweather et al. |

FOREIGN PATENT DOCUMENTS

| EP | 0 183 351 A1 | 6/1986 |
| EP | 1 281 351 A3 | 3/2004 |

(Continued)

OTHER PUBLICATIONS

International Preliminary Report on Patentability dated Jun. 23, 2011 as received in related application No. PCT/GB2009/051671, 9 pages.

(Continued)

*Primary Examiner* — Aarti B Berdichevsky
*Assistant Examiner* — Bradley Osinski
(74) *Attorney, Agent, or Firm* — Foley & Lardner LLP

(57) ABSTRACT

Diabetes management apparatus comprising a sensor providing measurements of glucose level in a human or animal; an insulin pump for delivering a dose of insulin to said human or animal; and a processor. The processor is adapted to perform the following steps: receive said measurements of glucose level from said sensor; calculate a insulin dose to be delivered by said insulin pump based on said received measurement; assess the validity of the status of the apparatus; and send a command to said insulin pump to deliver said calculated insulin dose, dependent on said assessing step confirming that the status is valid. The insulin pump is configured to deliver a preset dose of insulin unless said processor sends a command to said insulin pump and wherein a said command sent to said insulin pump is valid only for a predetermined time interval so that if no further commands are sent to said insulin pump during said predetermined time interval, said insulin pump reverts to delivering said preset dose of insulin at the end of said predetermined time interval.

15 Claims, 2 Drawing Sheets

Figure 1:
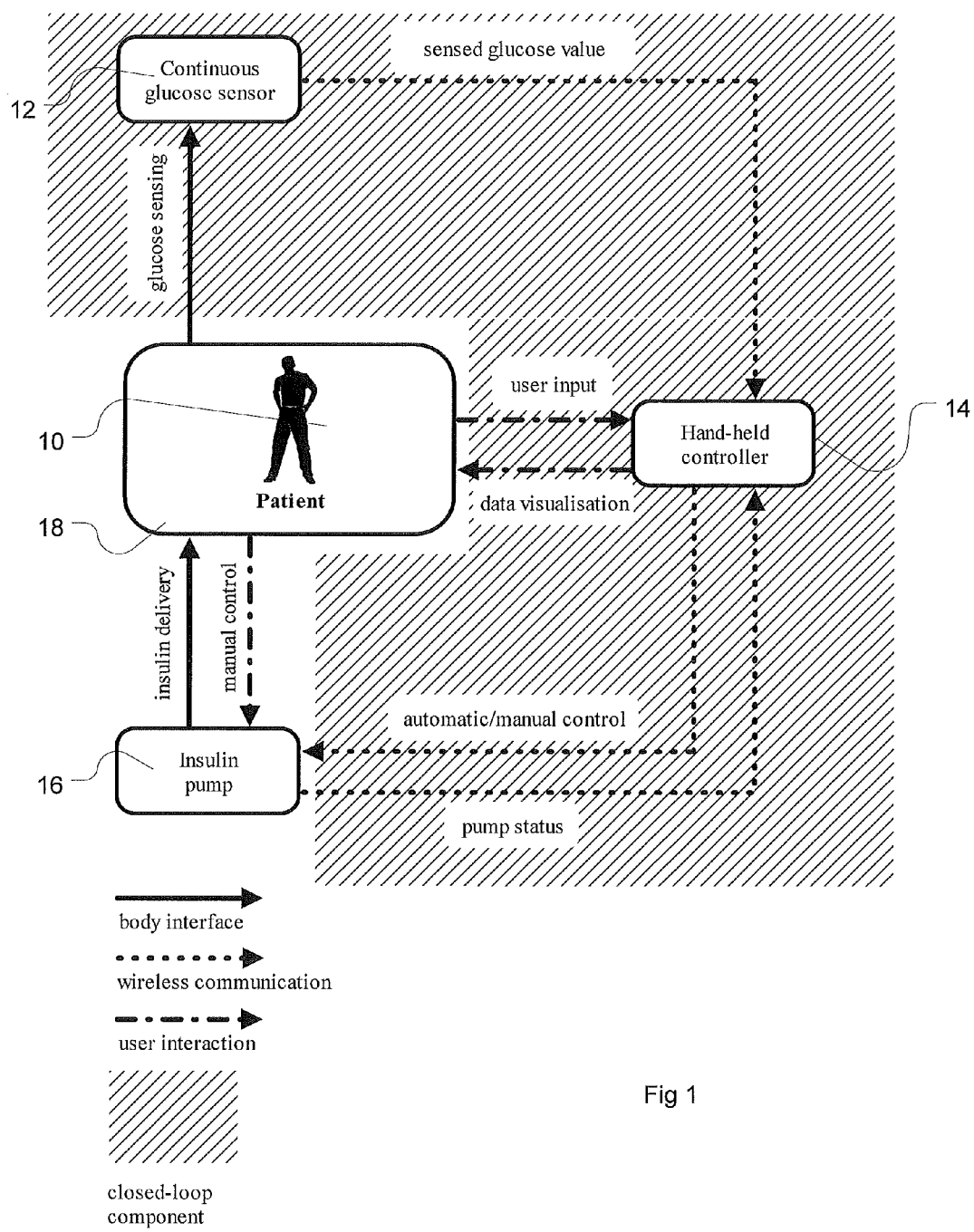

(51) Int. Cl.
  *A61M 5/172* (2006.01)
  *G06F 19/00* (2011.01)
  *A61M 5/142* (2006.01)
(52) U.S. Cl.
  CPC .. *G06F19/3468* (2013.01); *A61M 2005/14208* (2013.01); *A61M 2005/14296* (2013.01); *A61M 2205/3569* (2013.01); *A61M 2230/201* (2013.01)

(56) References Cited

FOREIGN PATENT DOCUMENTS

| EP | 0 939 602 | 9/2004 |
|---|---|---|
| WO | WO-97/15227 A1 | 5/1997 |
| WO | WO-2007/053832 A2 | 5/2007 |

OTHER PUBLICATIONS

"Standards of Medical Care in Diabetes," Diabetes Care, 28: S4-S36, 2005.
Hovorka R., "Continuous glucose monitoring and closed-loop systems," Diabetic Med. 23 (1):1-12, 2006.
Hovorka R., "Management of diabetes using adaptive control." Int. J. Adapt. Control 19 (5):309-326, 2005.
Hovorka R., Canonico V., Chassin LJ., Haueter U., Massi-Benedetti M, Orsini-Federici M. et al., "Non-linear model predictive control of glucose concentration in subjects with type 1 diabetes." Physiol Meas 2004; 25(4): 905-920.
International Search Report dated Mar. 20, 2009 as received in corresponding United Kingdom Application No. GB0822374.5, 3 pages.
International Search Report and Written Opinion dated Apr. 26, 2010 as received in corresponding PCT Application No. PCT/GB2009/051671, 14 pages.
Klonoff D. C., "Continuous Glucose Monitoring: Roadmap for 21st century diabetes therapy," Diabetes Care, 28: 1231-1239, 2005.
Lynch, SM and Bequette, BW., "Estimation-based model predictive control of blood glucose in type I diabetics: A simulation study." Proc of the IEEE 27th Annual Northeast Bioengineering Conference 2001; 79-80.
Palerm C. C., Zisser H., Bevier W. C., Jovanovic L., and Doyle III F. J., "Prandial insulin dosing using run-to-run control: application of clinical data and medical expertise to define a suitable performance metric." Diabetes Care 30 (5):1131-1136, 2007.
Parker RS, Doyle III FJ, Peppas NA, "A model-based algorithm for blood glucose control in type I diabetic patients." IEEE Trans Biomed Eng 1999; 46(2): 148-157.
Parker RS, Doyle III FJ, Peppas NA, "The intravenous route to blood glucose control." IEEE Eng Med Biol Mag 2001; 20(1): 65-73.
Pickup, J. and Keen, H., "Continuous subcutaneous insulin infusion at 25 years: evidence base for the expanding use of insulin pump therapy in type 1 diabetes," Diabetes Care, 25: 593-598, 2002.
Trajanoski Z. and Wach P., "Neural predictive controller for insulin delivery using the subcutaneous route." IEEE Trans Biomed Eng 1998; 45(9): 1122-1134.

* cited by examiner

SUBSTANCE MONITORING AND CONTROL IN HUMAN OR ANIMAL BODIES

CROSS-REFERENCE TO RELATED APPLICATIONS

This application is a National Stage application of PCT/GB2009/051671, filed Dec. 8, 2009, which claims priority from United Kingdom application 0822374.5, filed Dec. 8, 2008. The contents of both of the above applications is hereby incorporated by reference herein in its entirety.

This application relates to monitoring and controlling levels of substances, e.g. glucose, in human or animal bodies.

BACKGROUND

Diabetes is a group of heterogeneous chronic disorders characterised by hyperglycaemia due to relative or absolute insulin deficiency. Two major categories of diabetes are recognised according to aetiology and clinical presentation, type 1 diabetes and type 2 diabetes. More than 90% cases are accounted for by type 2 diabetes. Regional and ethnic differences in diabetes incidence and prevalence exist.

Type 1 diabetes is one of the most common chronic childhood disease in developed nations but occurs at all ages. Type 1 diabetes is caused by autoimmune destruction of pancreatic islet beta-cells resulting in the absolute loss of insulin production. Treatment demands the administration of exogenous insulin. Type 1 diabetes is associated with a high rate of complications normally occurring at young ages placing a considerable burden on the individual and the society.

In a healthy individual, insulin is secreted by the pancreas in a highly controlled fashion to maintain the plasma glucose concentration within a narrow physiological range. In type 1 diabetes, insulin is delivered exogenously to mimic the basal and postprandial insulin needs. The standard therapy is based on multiple insulin injections using a combination of short and long acting insulin analogues supported by blood glucose self-monitoring ("Standards of Medical Care in Diabetes," Diabetes Care, 28: S4-S36, 2005). Treatment by the continuous subcutaneous insulin infusion (CSII), i.e. using insulin pumps, is on the rise (J. Pickup and H. Keen, "Continuous subcutaneous insulin infusion at 25 years: evidence base for the expanding use of insulin pump therapy in type 1 diabetes," Diabetes Care, 25: 593-598, 2002).

The last two decades have witnessed unprecedented technological progress in the development of continuous glucose sensors (e.g. as described in EP0939602) resulting in the first generation of commercial glucose monitors (D. C. Klonoff, "Continuous Glucose Monitoring: Roadmap for 21st century diabetes therapy," Diabetes Care, 28: 1231-1239, 2005). This has fuelled the development of prototypes of a closed-loop system based on combination of a continuous monitor, a control algorithm, and an insulin pump (R. Hovorka. "Continuous glucose monitoring and closed-loop systems," Diabetic Med. 23 (1):1-12, 2006). These systems are normally termed an artificial pancreas.

As part of the artificial pancreas, the continuous glucose monitor could be an implantable or extracorporeal device and based on a minimally or non-invasive technology (D. C. Klonoff, "Continuous Glucose Monitoring: Roadmap for 21st century diabetes therapy," Diabetes Care, 28: 1231-1239, 2005). Generally, the implantable sensors are projected to have a lifespan of several months to years lifetime the non-implantable devices have, at present, a lifetime of one half day to several days.

Similarly, the insulin pump can be implanted or extracorporeal. The implantable pump normally delivers insulin intraperitoneally whereas the extracorporeal insulin pump delivers insulin subcutaneously.

The control algorithm can be implemented on a separate device, a patient monitor, or on the same platform as the insulin pump. The communication between the devices can be achieved using wire or wireless technologies. The latter are becoming prevalent for the transfer of data from insulin pumps onto diabetes management systems. Integrated systems exist which allow wireless transfer of data between glucose meters and insulin pumps such as the "all-in-one" CozMore™ Insulin Technology System (Smiths Medical MD, Inc, MN) or the Medtronic MiniMed Paradigm REAL-Time system (Northridge Calif., USA).

A wide spectrum of control algorithms has been proposed to titrate insulin in a closed-loop fashion, see a review by Parker et al (Parker R S, Doyle F J, III, Peppas N A. The intravenous route to blood glucose control. IEEE Eng Med Biol Mag 2001; 20(1): 65-73). For a clinical evaluation, two main categories have been employed, classical feedback control embodied in the proportional-integral-derivative (PID) controller, and model predictive control (MPC).

The principles of feedback control can be exemplified using the PID controller. The controller continuously adjusts the insulin infusion rate (IIR) by assessing glucose excursions from three viewpoints, the departure from the target glucose (the proportional component), the amount of time when glucose is different from the target glucose (the integral component), and the change in ambient glucose (the derivative component). IIR is computed as $$IIR = K_P(G - G_t) + K_I \int (G - G_t) + K_D \frac{dG}{dt}$$

where $K_P$, $K_I$, and $K_D$ represent weights (gains) given to the proportional, integral, and derivative components, and G and $G_t$ represent ambient and target glucose levels, respectively.

Tuning of the controller corresponds to the determination of constants $K_P$, $K_I$ and $K_D$. This can be achieved by an off-line assessment using, for example, pharmacokinetics modelling, or on-line using adaptive techniques. The constants can also be estimated from a subject's daily dose while the ratios between the constants remain the same.

The model predictive control is at the forefront of the recent research with contributions, for example, by Parker et al (Parker R S, Doyle F J, III, Peppas N A. A model-based algorithm for blood glucose control in type I diabetic patients. IEEE Trans Biomed Eng 1999; 46(2): 148-157), Lynch and Bequette (Lynch S M, Bequette B W. Estimation-based model predictive control of blood glucose in type I diabetics: A simulation study. Proc of the IEEE 27th Annual Northeast Bioengineering Conference 2001; 79-80), Trajanoski at al (Trajanoski Z, Wach P. Neural predictive controller for insulin delivery using the subcutaneous route. IEEE Trans Biomed Eng 1998; 45(9): 1122-1134), and Hovorka et al (Hovorka R, Canonico V, Chassin L J, Haueter U, Massi-Benedetti M, Orsini-Federici M et al. Non-linear model predictive control of glucose concentration in subjects with type 1 diabetes. Physiol Meas 2004; 25(4): 905-920). The MPC approach is most suitable for systems with long delays and open-loop characteristics and therefore well suited for the sc-sc approach with meal announcement.

The vital ingredient of the model predictive control is a model linking insulin delivery and possibly meal ingestion to glucose excursions. This can be a physiological model representing fundamental glucoregulatory processes or a "black-box" model disregarding the physiological insights but learning the insulin-glucose relationships using pattern recognition techniques. Both approaches can benefit from a wide range of models of the glucoregulatory system.

The development of the MPC controller consists of selecting a suitable model, obtaining model parameters, and deciding on other elements such as the length of the prediction window and the form of the target trajectory. Adaptive techniques allow model parameters to be individualised either off- or on-line.

Apart from being used as part of a closed-loop system, continuous glucose monitoring can also be used on retrospective basis to optimise insulin delivery in an open-loop algorithm-based treatment modification (R. Hovorka. Management of diabetes using adaptive control. Int. J. Adapt. Control 19 (5):309-326, 2005; C. C. Palerm, H. Zisser, W. C. Bevier, L. Jovanovic, and F. J. Doyle, III. Prandial insulin dosing using run-to-run control: application of clinical data and medical expertise to define a suitable performance metric. Diabetes Care 30 (5):1131-1136, 2007). It can also be used by the patient to deliver a correction insulin bolus, to modify temporarily the delivery of insulin via the insulin pump, to warn of impeding too low or too high glucose level, or to take other diabetes management actions.

In summary, continuous glucose monitor can be used as a part of a closed-loop system with automated insulin delivery or as a part of open-loop system for retrospective data evaluation or real-time sporadic management interventions initiated by the patient or his/her career.

STATEMENTS OF INVENTION

According to the invention there is provided diabetes management apparatus comprising:
a sensor providing measurements of glucose level in a human or animal;
an insulin pump for delivering insulin to said human or animal; and
a processor which is adapted to perform the following steps:
receive said measurements of glucose level from said sensor;
calculate an insulin dose to be delivered by said insulin pump based on said received measurement;
confirm the validity of the status of the apparatus;
send a command to said insulin pump to deliver said calculated insulin dose, dependent on confirmation that the status of the apparatus is valid; and
repeat said receiving, calculating, confirming and sending steps,
wherein said insulin pump is configured to deliver a preset dose of insulin unless said processor sends a command to said insulin pump and wherein a said command sent to said insulin pump is valid only for a predetermined time interval so that if no further commands are sent to said insulin pump during said predetermined time interval, said insulin pump reverts to delivering said preset dose of insulin at the end of said predetermined time interval.

In other words, the apparatus is configured to operate in open-loop mode when no command is provided to the insulin pump by the processor. In this open-loop mode, the preset dose may a pre-programmed continuous infusion rate of insulin or may be a insulin bolus or series of insulin boluses applied under the control of a patient or health-care provider. When the processor is providing commands, the apparatus may be termed in closed-loop mode. The predetermined time interval may be termed the "temporal closed-loop interval" and may have a duration of five, ten, fifteen, or eighteen minutes. If only one command is sent, the apparatus operates in closed-loop mode only for the duration of this interval. In contrast to other prior art systems, notably that of EP 0939602, the default setting of the system is thus open-loop mode. This approach also exploits the existing feature of smart insulin pumps by using the temporary setting of the insulin infusion rate.

The apparatus is configured so that if, during said predetermined time interval, the processor sends a further command having a further associated predetermined time interval to said insulin pump to deliver a further calculated insulin dose, said insulin pump delivers said further calculated insulin dose until the end of said further associated predetermined time interval if no additional commands are sent to said insulin pump during said further predetermined time interval. In other, the sending of another command resets the temporal closed-loop interval.

Where the preset dose is a continuous infusion rate, the command sent by the processor may alter, e.g. increase or decrease, a preset insulin infusion rate. Alternatively, the command may turn off the preset insulin infusion rate and initiate an insulin bolus or a series of insulin boluses. Alternatively, the command may alter the preset insulin infusion rate and initiate an insulin bolus. Where the preset dose is an insulin bolus or a series of insulin boluses, the command sent by the processor may stop said insulin bolus(es) and deliver a continuous infusion rate and/or one or more boluses as determined by the processor.

The processor may be configured to confirm the validity of the system by assessing whether or not any one of the following conditions is satisfied:
the sensor is providing valid and/or not corrupted glucose measurements.
the sensor is communicating correctly with the processor
the insulin pump is correctly delivering insulin.

The apparatus may comprise more than one sensor which may or may not measure glucose. Where there are a plurality of glucose sensors, the processor may be configured to confirm the validity of the system by assessing the concordance of the readings from the plurality of glucose sensors. Where there is a non-glucose sensor measuring a non-glucose substance, e.g. ketone bodies, the processor may be configured to confirm the validity of the system by assessing the measurements from the non-glucose sensor. Ketone bodies may be used to detect the interruption of insulin delivery, e.g. due to failure of the insulin pump.

If the processor determines that the status of the apparatus is not valid, the processor may be configured to immediately stop sending further commands to the insulin pump. Alternatively, the processor may be configured to continue sending further commands for another predetermined time interval.

If the processor determines that the status of the apparatus is not valid, the processor may be configured to attempt to recover by re-assessing the status for a predetermined time interval. Once this interval lapses, the processor may raise an alarm to notify the patient that the apparatus is operating in open loop mode. If the processor is able to re-establish the validity of the status of the apparatus, it may re-enter closed loop insulin delivery without notifying the patient about the interruption in closed loop insulin delivery.

The apparatus may further comprise a monitor for displaying information to a patient and/or for inputting information from a patient. The information from the patient may include instructions to operate in a particular mode and thus the processor may be configured to check for such instructions when confirming the validity of the system.

The communication between the components, e.g. glucose sensor, controller, insulin pump and/or patient monitor may be via any suitable communication, e.g. via wire-based or wireless communication.

The at least one glucose sensor may be implanted or extracorporeal. The at least one glucose sensor may be a subcutaneous, intravascular or intradermal glucose sensor. There may be a plurality of glucose sensors which may be of the same or different type. The insulin pump may be implanted or extracorporeal. The insulin pump may deliver insulin subcutaneously, intravenously or intraperitoneally.

The controller, insulin pump and patient monitor may be separate components. However, the same functionality may be achieved if one or more of these components are integrated together. For example, the controller and/or insulin pump may be integrated into the patient monitor.

According to another aspect of the invention there is a method of controlling diabetes comprising:
 measuring glucose levels in a human or animal;
 delivering insulin to said human or animal; and
 controlling said delivery of insulin by performing the following steps:
  calculating an insulin dose to be delivered based on said measurements;
  performing a status integrity check;
  issuing a command to deliver said calculated insulin dose, dependent on confirmation that said status integrity check is valid;
  wherein a said issued command is valid only for a predetermined time interval so that if no further commands are issued during said predetermined time interval, said insulin delivery reverts to a preset dose of insulin at the end of said predetermined time interval.

The invention further provides processor control code to implement the above-described methods, in particular on a data carrier such as a disk, CD- or DVD-ROM, programmed memory such as read-only memory (Firmware), or on a data carrier such as an optical or electrical signal carrier. Code (and/or data) to implement embodiments of the invention may comprise source, object or executable code in a conventional programming language (interpreted or compiled) such as C, or assembly code, code for setting up or controlling an ASIC (Application Specific Integrated Circuit) or FPGA (Field Programmable Gate Array), or code for a hardware description language such as Verilog (Trade Mark) or VHDL (Very high speed integrated circuit Hardware Description Language). As the skilled person will appreciate such code and/or data may be distributed between a plurality of coupled components in communication with one another.

FIGURES

Figure 2:
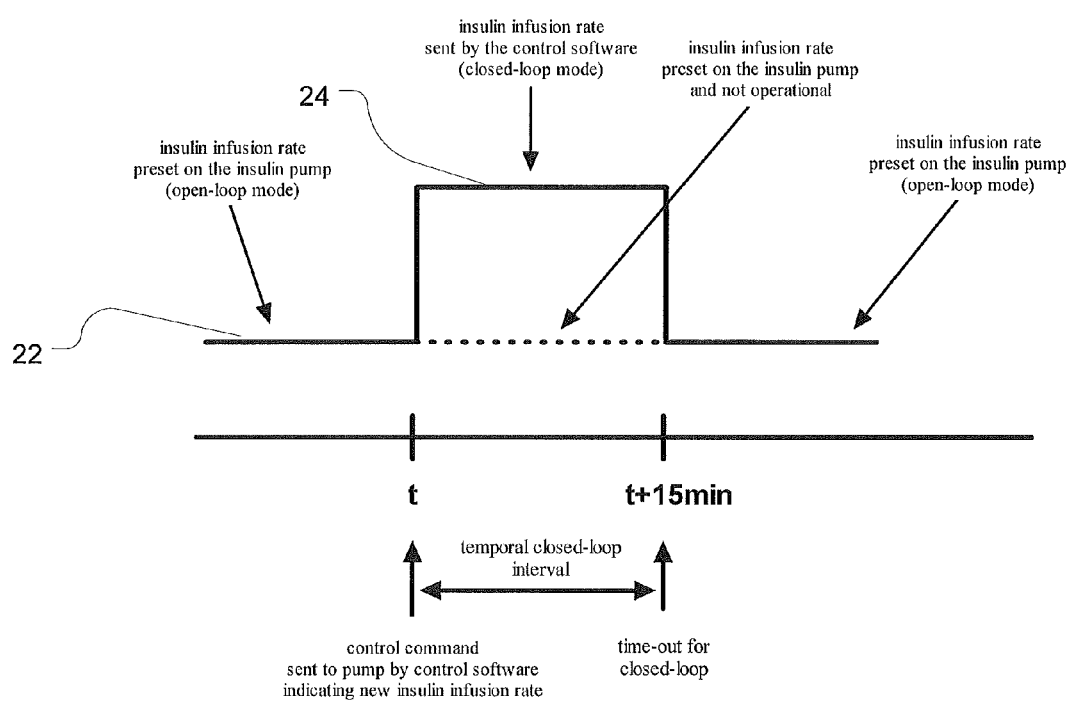

FIG. 1 is an overview of a hybrid closed-loop system, and
FIG. 2 shows the change of the insulin infusion rate with time when switching between open-loop mode and closed loop mode.

FIG. 1 shows a hybrid open loop and closed loop system for a patient 10 suffering from diabetes. The system comprises at least one continuous glucose sensor 12 which takes glucose readings, e.g. as a time series of measurement taken at regular time intervals over a period of time, from the patient 10 using a body interface. The glucose sensor 12 may an implantable or extracorporeal device. The sensed glucose values pass to a processor or controller 14 running control software described in more detail below. The controller 14 may send data to a patient monitor 18 for visualisation on a screen. Optionally, the patient may also input information to the controller using the patient monitor 18. The controller 14 also communicates with an insulin pump 16 as described in relation to FIG. 2. The insulin pump 16 sends pump status information to the controller 14. The insulin pump 16 may an implantable or extracorporeal device and delivers insulin to the patient via a body interface. The insulin pump 16 may also be manually controlled by the patient 10. Communication between the controller, patient monitor and insulin pump may be via any suitable method, including wireless communication.

The sensor 12, controller 14 and insulin pump 16 together form the closed loop components. In open loop mode, the insulin pump is the only component of the closed loop mode which must be operational. The patient monitor 18 and sensor 12 may be operational, e.g. to provide information to the patient to self-administer insulin. The controller 14 is not operational in the open loop mode. In FIG. 1, the controller 14, insulin pump 16 and patient monitor are depicted as separate components. However, the same functionality may be achieved if one or more of these components are integrated together. For example, the controller and/or patient monitor may be integrated into the insulin pump.

The system operates in an open-loop mode until the insulin pump 16 receives a control command from the controller 14 and the system enters into a closed-loop mode. FIG. 2 shows the change of the insulin infusion rate when switching between open-loop mode and closed loop mode. Initially, the insulin infusion rate is at a preset level 22. When a command is received to initiate the closed loop mode at time t, there is a step change to a higher insulin rate 24. For ease of reference, the preset level is shown in dashed line. As illustrated, this control command has temporal validity for 15 mins (clearly other time periods may be defined). At the end of the time period, if no other control commands are received, the insulin infusion rate returns to the preset value 22 for the open-loop mode at the end of the temporal closed-loop interval. Alternatively, if a new control command is received during the temporal closed-loop interval, e.g. at time $t_2$ which is between t and t+15, the pump is set to a new insulin infusion rate. The start of the temporal closed-loop interval is reset to the time $t_2$ when the control command was received by the insulin pump so that the new temporal validity period expires at $t_2$+15.

A control command is not submitted by the controller to the insulin pump when any or a subset of the following conditions occurs:
 User selects "open mode" operation for the system (e.g. using the patient monitor to input this operation to the controller)
 Glucose sensor information is not available to the control software (e.g. due to malfunction of the sensor or communication between the sensor and controller).
 Glucose sensor data is corrupted or not valid either at the point of detection or when transmitted (e.g. when the continuous glucose sensor requires calibration)
 The control software detects unusual physiological conditions such as a sudden increase in insulin resistance indicating, for example, interrupted insulin delivery due to dislodged insulin needle
 The control software detects a large discrepancy in glucose readings by two or more continuous glucose sensors concurrently measuring glucose concentrations in a single subject
 The clock time of the control software is outside the preset period(s) for closed loop operation of the system, e.g. the controller is programmed with a preferred operation for different times of day, including for example open loop operation at meal times.

Where glucose sensor information is not available or is corrupted/not valid; the system may be considered to fail an integrity check. For such failures, the controller may be programmed to continue sending control commands for a predetermined time period, e.g. 15 min, 30 min, 45 min or 60 min. However, if failures continue longer than this predetermined period, the system defaults to open loop mode. Even when in open loop, the controller continues to check the system integrity and if the system integrity is restored, e.g. information becomes available or is no longer corrupted/not valid; the controller issues a command and the system changes to closed loop mode.

No doubt many effective alternatives will occur to the skilled person. It will be understood that the invention is not limited to the described embodiments and encompasses modifications apparent to those skilled in the art lying within the spirit and scope of the claims appended hereto.

The invention claimed is:

1. A hybrid open and closed loop diabetes management apparatus comprising:
a sensor providing measurements of glucose level in a human or animal when the apparatus is operating in a closed-loop mode for a predetermined time interval;
an insulin pump for delivering both of:
a preset dose of insulin to said human or animal when the apparatus is operating in an open-loop mode, wherein said open-loop mode is a default setting of said apparatus, and
a calculated insulin dose to said human or animal when the apparatus is operating in said closed-loop mode for said predetermined time interval; and
a processor which is adapted to perform the following steps:
receive said measurements of glucose level from said sensor;
calculate said calculated insulin dose to be delivered by said insulin pump in said closed-loop mode based on said received measurement;
assess the validity of the status of the apparatus; and
send a command to said insulin pump to enter said closed-loop mode for said predetermined time interval and deliver said calculated insulin dose during said predetermined time interval, dependent on said assessing step confirming that the status is valid,
wherein said apparatus is configured to operate in said default open-loop mode wherein said insulin pump is configured to deliver said preset dose of insulin unless said processor sends said command to said insulin pump so that said apparatus is configured to operate in said closed-loop mode, and
wherein the command sent to said insulin pump is valid only for said predetermined time interval so that if no further commands are sent to said insulin pump during said predetermined time interval, said insulin pump reverts to said open-loop mode delivering said preset dose of insulin at the end of said predetermined time interval.

2. A hybrid open and closed loop diabetes management apparatus according to claim 1, wherein the preset dose is a pre-programmed continuous infusion rate of insulin and said processor is configured to send a command which alters said continuous infusion rate.

3. A hybrid open and closed loop diabetes management apparatus according to claim 2, wherein the predetermined time interval has a duration of five, ten, fifteen, or eighteen minutes.

4. A hybrid open and closed loop diabetes management apparatus according to claim 1, wherein the predetermined time interval has a duration of five, ten, fifteen, or eighteen minutes.

5. A hybrid open and closed loop diabetes management apparatus according to claim 1, wherein the processor is configured to confirm the validity of the system by assessing whether or not the sensor is providing valid and/or not corrupted glucose measurements.

6. A hybrid open and closed loop diabetes management apparatus according to claim 1, wherein the processor is configured to confirm the validity of the system by assessing whether or not the sensor is communicating correctly with the processor.

7. A hybrid open and closed loop diabetes management apparatus according to claim 1, wherein the processor is configured to confirm the validity of the system by assessing whether or not the insulin pump is correctly delivering insulin.

8. A hybrid open and closed loop diabetes management apparatus according to claim 1, comprising more than one sensor.

9. A hybrid open and closed loop diabetes management apparatus according to claim 8, comprising a plurality of glucose sensors and wherein the processor is configured to confirm the validity of the system by assessing the concordance of the readings from the plurality of glucose sensors.

10. A hybrid open and closed loop diabetes management apparatus according to claim 8, comprising a non-glucose sensor measuring a non-glucose substance and wherein the processor is configured to confirm the validity of the system by assessing the measurements from the non-glucose sensor.

11. A hybrid open and closed loop diabetes management apparatus according to claim 1, wherein the processor is configured to confirm the validity of the system by determining the preferred operational mode for the time of day.

12. A hybrid open and closed loop diabetes management apparatus according claim 1, further comprising a monitor for displaying information to a patient and/or for inputting information from a patient.

13. A hybrid open and closed loop diabetes management apparatus according to claim 12, wherein said processor is integrated in said monitor.

14. A computer-implemented method of controlling a hybrid open and closed loop diabetes management apparatus, the method comprising the steps of:
delivering both of:
a pre-set dose of insulin to a human or animal when the apparatus is operating in an open-loop mode, wherein said open-loop mode is a default setting of said apparatus, and
a calculated insulin dose to said human or animal when the apparatus is operating in a closed-loop mode for a predetermined time interval;
controlling said delivery of insulin in said closed-loop mode by performing the following steps:
calculating said calculated insulin dose to be delivered in said closed-loop mode based on measurements of glucose levels in said human or animal;
performing a status integrity check;
issuing a command to enter said closed-loop mode for said predetermined time interval and deliver said calculated insulin dose during said predetermined time interval, dependent on confirmation that said status integrity check is valid;

wherein the issued command is valid only for said predetermined time interval so that if no further commands are issued during said predetermined time interval, said insulin delivery reverts to said open-loop mode delivering said preset dose of insulin at the end of said predetermined time interval.

15. A carrier carrying computer program code to, when running, implement the method of claim 14.

* * * * *